US 9,439,560 B2

(12) United States Patent
Hakanen et al.

(10) Patent No.: US 9,439,560 B2
(45) Date of Patent: Sep. 13, 2016

(54) LARYNGOSCOPE

(71) Applicant: CareFusion Corporation, San Diego, CA (US)

(72) Inventors: Jukka Antti Petteri Hakanen, Espoo (FI); Alan George Furler, Sparta, NJ (US); Jeremy Michael Ross, New York, NY (US); Petri Tapio Pikkarainen, Helsinki (FI); Lauri Artturi Lumme, Oulu (FI); Mika Kristian Henriksson, Kempele (FI)

(73) Assignee: CAREFUSION CORPORATION, San Diego, CA (US)

( * ) Notice: Subject to any disclaimer, the term of this patent is extended or adjusted under 35 U.S.C. 154(b) by 180 days.

(21) Appl. No.: 13/793,610

(22) Filed: Mar. 11, 2013

(65) Prior Publication Data

US 2013/0190568 A1    Jul. 25, 2013

Related U.S. Application Data

(63) Continuation of application No. 12/822,841, filed on Jun. 24, 2010, now Pat. No. 8,414,481.

(51) Int. Cl.
*A61B 1/267* (2006.01)
*A61B 1/06* (2006.01)

(52) U.S. Cl.
CPC *A61B 1/267* (2013.01); *A61B 1/06* (2013.01)

(58) Field of Classification Search
CPC ... A61B 1/267; A61B 1/2673; A61B 1/2676
USPC .................................. 600/101–200, 218–225
See application file for complete search history.

(56) References Cited

U.S. PATENT DOCUMENTS

| 4,573,451 A | 3/1986 | Bauman |
| 5,800,344 A | 9/1998 | Wood, Sr. et al. |
| 6,142,144 A | 11/2000 | Pacey |
| 6,543,447 B2 | 4/2003 | Pacey |
| 6,655,377 B2 | 12/2003 | Pacey |
| 7,156,091 B2 | 1/2007 | Koyama et al. |
| 2003/0168059 A1 | 9/2003 | Pacey |

(Continued)

FOREIGN PATENT DOCUMENTS

| GB | 2086732 | 5/1982 |
| WO | WO-9104703 | 4/1991 |

(Continued)

OTHER PUBLICATIONS

Partial Search Report from corresponding GB Application No. GB1110346.2, dated Oct. 11, 2011.

(Continued)

*Primary Examiner* — Ellen C Hammond
*Assistant Examiner* — Christina Negrellirodrigue
(74) *Attorney, Agent, or Firm* — McDermott Will & Emery LLP

(57) ABSTRACT

A laryngoscope includes an arm and a handle. The arm is configurable between at least a first and a second position. A first blade sheath secures over the arm in the first position and a second blade sheath secures over the arm in the second position. A method of configuring a laryngoscope includes configuring a laryngoscope arm into a first position or a second position and securing a selected blade sheath to the arm.

20 Claims, 9 Drawing Sheets

(56) References Cited

U.S. PATENT DOCUMENTS

| | | | |
|---|---|---|---|
| 2005/0234303 A1* | 10/2005 | McMorrow | A61B 1/267 600/189 |
| 2006/0276693 A1 | 12/2006 | Pacey | |
| 2007/0135687 A1 | 6/2007 | Balas | |
| 2007/0167686 A1 | 7/2007 | McGrath | |
| 2008/0045801 A1* | 2/2008 | Shalman | A61B 1/267 600/193 |
| 2008/0146879 A1 | 6/2008 | Pacey | |
| 2010/0261967 A1 | 10/2010 | Pacey et al. | |
| 2010/0261968 A1* | 10/2010 | Nearman | A61B 1/00041 600/188 |

FOREIGN PATENT DOCUMENTS

| | | |
|---|---|---|
| WO | WO-9819589 | 5/1998 |
| WO | WO-9944490 | 9/1999 |
| WO | WO-03041570 | 10/2003 |
| WO | WO-2007066134 | 6/2007 |
| WO | WO-2008157170 | 12/2008 |

OTHER PUBLICATIONS

Search Report from corresponding GB1110346.2, dated Mar. 7, 2012.

First unbreakable plastic blade—easy choice for EMS providers and anesthesiologists; MSVision endoscopy solutions; http://www.ms-vision.com/Technology.aspx?PageId=2; Sep. 16, 2010.

McGrath® Video Laryngoscope; Series 5 HLDi; Designed & manufactured by Aircraft medical; MA North America, Inc.; 2009.

Karl Storz Remote Visual Inspection Products; www.karlstorz.com; pp. 1-8; 2009.

GlideScope Video Laryngoscopes Cobalt; Designed for $1^{st}$ Pass Success; Verathan Medical; 2010.

GlideScope Video Laryngoscopes GlideRite Stylets; Designed for $1^{st}$ Pass Success; Verathon Medical; 2010.

Chinese Notification to Grant Patent Right for Invention for Chinese Patent Application No. 201010623473.9, dated Apr. 9, 2015, 4 pages.

* cited by examiner

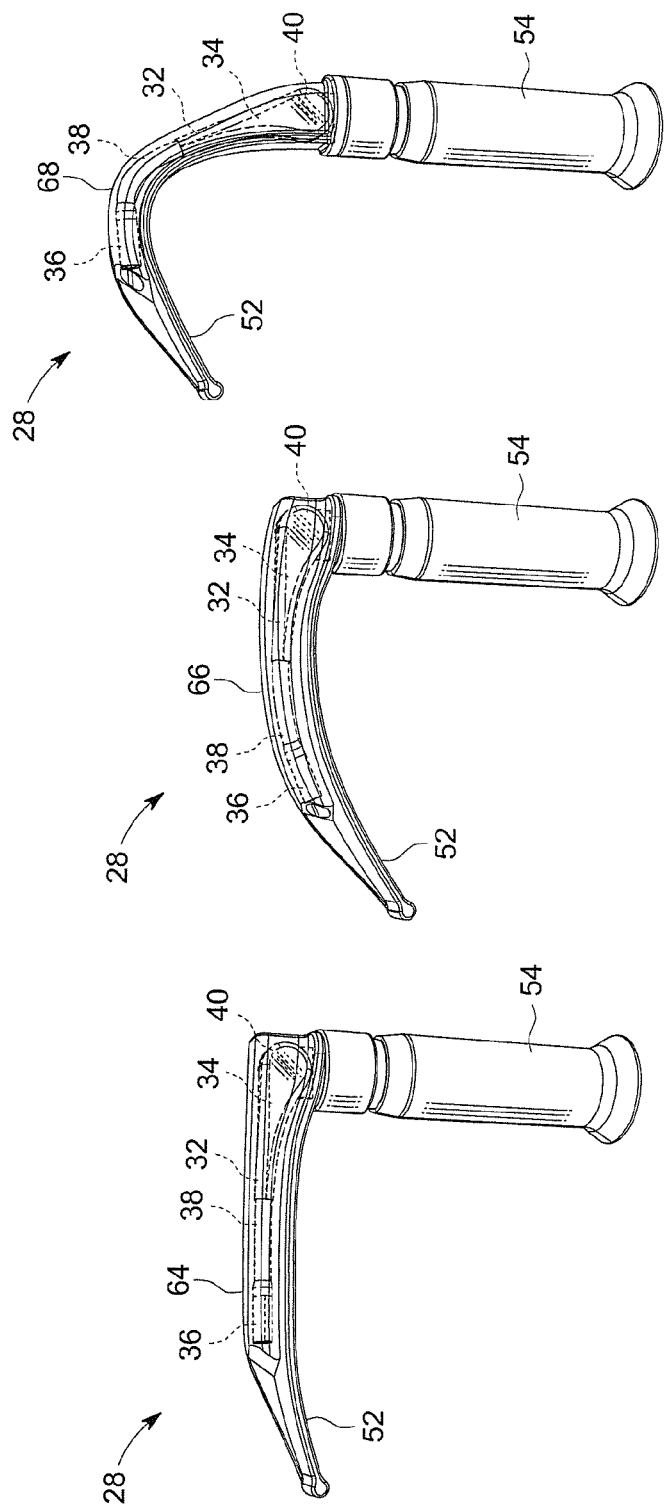

LARYNGOSCOPE

CROSS REFERENCE TO RELATED APPLICATION

The present application is continuation of U.S. patent application Ser. No. 12/822,841, filed Jun. 24, 2010, the contents of which are incorporated herein by reference in their entireties.

BACKGROUND

The present disclosure relates to a laryngoscope to be inserted inside a patient's mouth. More specifically, the laryngoscope is configured for use in both direct and indirect laryngoscopy.

When a patient is unconscious, for example, during general anesthesia, it is necessary to maintain a patient's airway. This can be done with an endotracheal tube that is inserted in the patient's trachea. A properly placed endotracheal tube establishes an open path for air into the patient's lungs. One of the difficulties with intubation is making sure that the endotracheal tube is inserted in the patient's trachea, which leads to the lungs, rather than in the esophagus which leads to the patient's stomach. The tool used to visually verify the placement of the endotracheal tube is called a laryngoscope and the observation of a patient's throat using a laryngoscope is referred to as laryngoscopy. The procedure of fitting an endotracheal tube in the patient's trachea is often called intubation.

A laryngoscope includes a handle and a blade. In use, the blade is inserted inside the patient's mouth and partially down the patient's throat to create a direct line of sight to the vocal chords. The blade applies pressure to soft tissue of the throat as well as aligns the patient's head and neck in order to create this direct line of sight. This is called direct laryngoscopy. An intubation performed during direct laryngoscopy is referred to as a direct intubation.

In some clinical settings, the patient's limited neck mobility may not allow the patient's head and/or neck to be manipulated enough to create the line of sight to the vocal chords required in direct laryngoscopy. A video laryngoscope is a modified laryngoscope used for indirect laryngoscopy. The video laryngoscope combines a generally curved blade with a camera disposed at the distal end. The curved blade can be inserted in the patient's mouth and throat with minimal neck movement and the camera is connected to a graphical display that provides the caregiver with the visual confirmation required for proper endotracheal tube placement. Indirect laryngoscopy is usually used for difficult intubation but is applicable for non-difficult or "routine" intubations as well.

BRIEF DISCLOSURE

A laryngoscope includes a handle, a first arm component, and a second arm component. A camera is disposed at an end of the second arm component. An intermediate arm component movably connects the first arm component to the second arm component. A hinge pivotally connects the handle to the first arm component. The first arm component is pivotable about the hinge between at least a first position and a second position.

In an alternative embodiment, the laryngoscope includes a substantially rigid handle defining an open interior. A power source is housed within the open interior of the substantially rigid handle. A first arm component is pivotally connected to the handle by a hinge. A second arm component is movably connected to the first arm component by an intermediate arm component. A camera is disposed at one end of the second arm component.

The camera is electronically coupled to the power source. A blade sheath is configured with an open interior for receiving the second arm component, intermediate arm component, first arm component, and hinge. The blade sheath sealingly engages the substantially rigid handle to form a fluid impervious seal connecting the open interiors of the substantially rigid handle and the blade sheath.

A method of configuring a laryngoscope prior to a laryngoscopy as disclosed herein includes providing a laryngoscope structure including a handle, a hinge connected to the handle, a first arm component pivotally connected to the hinge, and the second arm component pivotally connected to the first arm component. The handle is secured within a handle sheath. The first arm component is pivoted about the hinge between a first position and a second position. The first position establishes a substantially perpendicular geometry between the first arm component and the handle. The second position establishes a substantially obtuse geometry between the first arm component and the handle. A blade sheath, selected from a plurality of blade sheaths, is secured over the first arm component, second arm component, and the hinge, wherein the selected blade sheath engages the handle sheath in a fluid seal engagement. If the laryngoscopic procedure is a direct laryngoscopy, the first arm component is pivoted into the first position and a substantially flat blade sheath is selected from the plurality of blade sheaths. If the laryngoscopy procedure is an indirect laryngoscopy, the first arm component is pivoted into the second position and a substantially curved blade sheath is selected from the plurality of blade sheaths.

BRIEF DESCRIPTION OF THE DRAWINGS

FIG. 4A-C depict laryngoscopes with varying blade sheaths;

DETAILED DISCLOSURE

Figure 1:
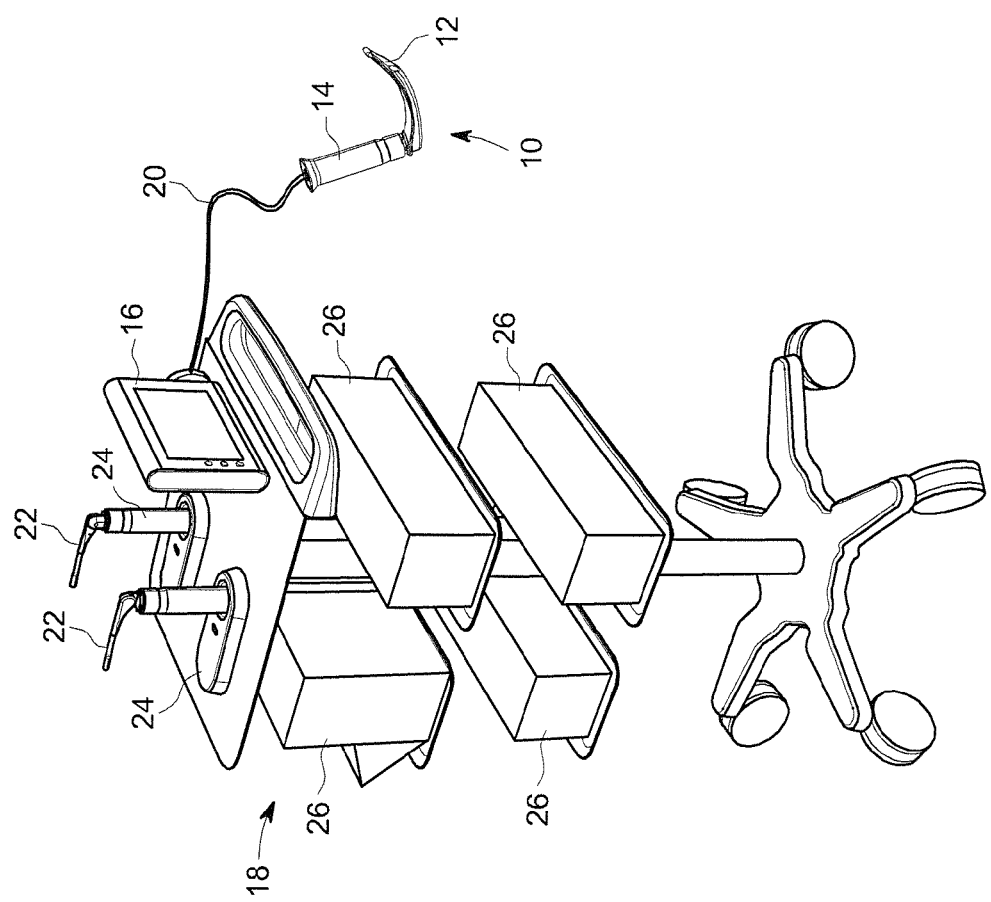
FIG. 1 is an environmental view with an embodiment of a laryngoscope.

FIG. 1 depicts an environmental view of an embodiment of a laryngoscope 10. The laryngoscope 10 generally includes a blade 12 and a handle 14. In the embodiment depicted in FIG. 1, the laryngoscope 10 is a video laryngoscope and therefore is connected to a graphical display 16. The graphical display 16, as well as the laryngoscope 10, may be transported on a cart 18, such that the equipment may be moved about a medical care facility to a location where it is presently needed.

The laryngoscope 10 is connected to the graphical display 16 by a data connection 20. While the data connection 20 is depicted as a wired connection between the laryngoscope 10 and the graphical display 16, it is understood that alternative types of data connections, including wireless data connections (e.g. RF and infrared) are within the scope of the present disclosure.

The cart 18 may further include one or more additional laryngoscopes 22. As will be disclosed in further detail herein, the laryngoscopes 22 may be battery operated, and therefore charging stands 24 integrated with the cart 18 may provide recharging capability to the laryngoscopes 22, when they are not in use. Further, as will be disclosed in greater detail herein, the laryngoscope 10 may be used with a plurality of blade sheaths and therefore and cart 18 may include supplies 26 of a plurality of different blade sheath types.

Figure 2:
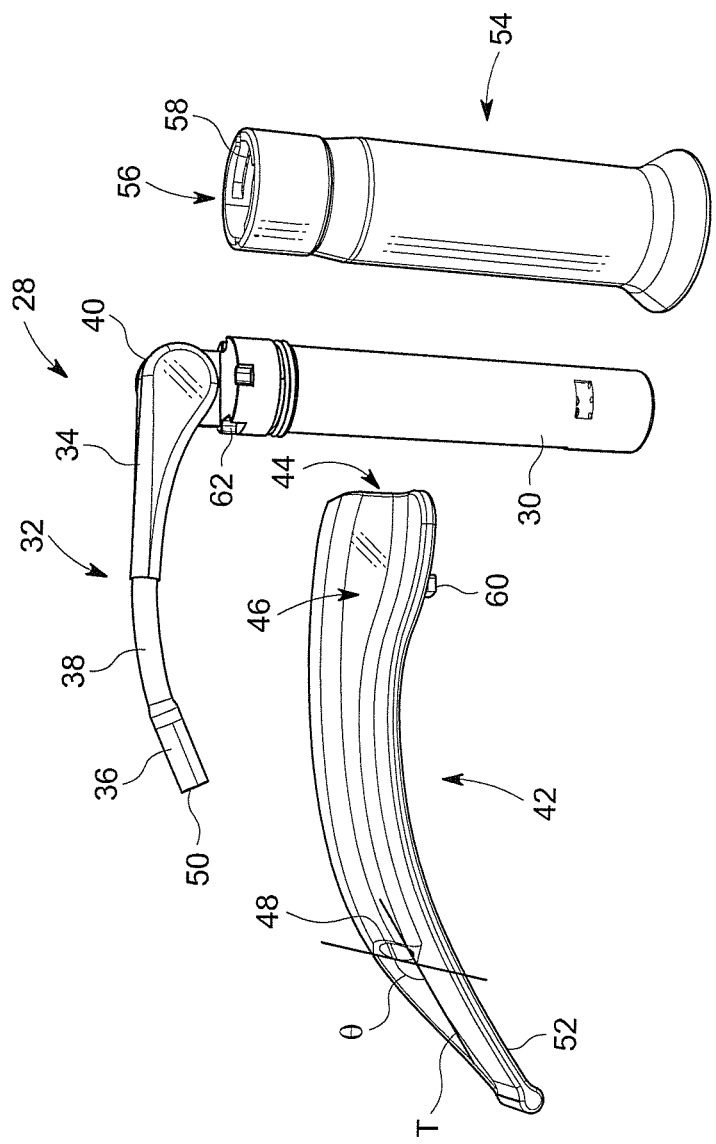
FIG. 2 depicts a first embodiment of a laryngoscope.

FIG. 2 depicts an embodiment of a laryngoscope 28. The laryngoscope 28 includes a handle 30 and an arm 32. The arm 32 includes a first arm component 34 at a proximal end of the arm 32. The arm 32 further includes a second arm component 36 at a distal end of the arm 32. The first arm component 34 and the second arm component 36 are both substantially rigid in construction. The first arm component 34 is movably connected to the second arm component 36 by an intermediate arm component 38.

In the embodiment of the laryngoscope 28 depicted in FIG. 2, the intermediate arm component 38 is a flexible component that facilitates the pivotal movement of the second arm component 36 with respect to the first arm component 34.

In an embodiment, the first arm component 34 is approximately 50% of the length of arm 32. The second arm component 36 is approximately 20% of the length of the arm 32. The intermediate arm component 38 is approximately 30% of the length of the arm 32. This construction of the arm 32 places the substantially rigid first and second arm components 34, 36 at locations to support and strengthen the blade sheaths as disclosed further herein, while provides for articulation of the arm 32. Articulation of the arm 32 allows for the arm 32 to be configured to fit a variety of blade sheaths, as will be disclosed in greater detail herein.

The first arm component 34 and the second arm component 36 are attached to the intermediate arm component 38 in a variety of attachment configurations, including, but not limited to, threaded engagement, ultrasonic welding, and coaxial engagements; however, this is not intended to be limiting and there are many other suitable engagements between these components as would be recognized by one of ordinary skill in the art.

The first arm component 34 is connected to the handle 30 by a hinge 40. The hinge 40 facilitates pivotal movement by the first arm component 34 with respect to the handle 30, about the hinge 40. Embodiments of the hinge 40 include a locking mechanism (not depicted) such as a tab or a spring that allows the hinge 40 to releasably lock in a plurality of positions.

The laryngoscope 28 further includes a blade sheath 42. The blade sheath 42 may be of a disposable or of a reusable construction. If the blade sheath 42 is of a reusable construction, the blade sheath 42 is autocleavable. The blade sheath 42 is constructed from a biocompatible material, of which a non-limiting example may be polyvinylchloride (PVC) plastic. While the embodiment of the blade sheath 42 depicted in FIG. 2 has a generally flat geometry as will be disclosed in greater detail, it is understood that this is not to be limiting in the scope of blade sheath geometries that may be used with embodiments of the laryngoscope 28. Exemplary alternative blade sheath geometries are described in greater detail herein with respect to FIGS. 4A-4C.

The blade sheath 42 includes an open end 44. The open end 44 opens to an open interior 46 within the blade sheath 42. The open end 44 and the open interior 46 are configured to slidably receive the arm 32 of the laryngoscope 28, including the first arm component 34, the second arm component 36, the intermediate arm component 38, and the hinge 40. The first arm component 34 is pivoted about the hinge 40 and the second arm component 36 is pivoted about the intermediate component 38 such as to configure the arm 32 into a shape to be received in the open interior 46 of the blade sheath 42. As disclosed above, the first arm component 34 and the second arm component 36 are both of a substantially rigid construction and the dimensions of the first arm component 34 and the second arm component 36 are of such with respect to the blade sheath such that the substantially rigid first arm component 34 and second arm component 36 provide strength and rigidity to the blade sheath 42. Such qualities of strength and rigidity are desirable in embodiments of the blade sheath 42 such as to facilitate the performance of a laryngoscopy.

A window 48 is located at an opposite end of the open interior 46 from the open end 44. The window 48 closes the open interior 46 at a location about a distal end 50 of the second arm component 36, when the arm 32 is fully received within the open interior 46. The window 48 is positioned at an angle θ with respect to a local tangent T of the blade sheath 42. Angle θ is a generally obtuse angle of at least 90° or greater. The angle θ of the window 48 is selected to serve the functions of inhibiting the build up of blood, mucous, or other fluids on the window 48, as well as to minimize light distortion and refraction through the window 48.

An elongated end 52 extends past the open interior 46 and the window 48 at the distal end of the blade sheath 42. The elongated end 52 is configured for engagement with soft tissue of the patient's throat, as will be described in greater detail herein with respect to various blade geometries.

The laryngoscope 28 further includes a handle sheath 54. The handle sheath 54 is of a disposable or reusable construction. If the handle sheath 54 is of a reusable construction, then the handle sheath is autocleavable. The handle sheath 54 may be constructed of a material similar to that of the blade sheath 42, which may include PVC.

The handle sheath 54 includes an open interior 56 that is configured to coaxially receive the handle 30.

The handle sheath 54 further includes one or more grooves 58 along an inner circumference of the handle sheath 54. The grooves 58 are configured to mate with and slidably engage one or more tabs 60 dependent from the blade sheath 42. The handle 30 further includes one or more recesses 62 in the outer periphery of a top end of the handle 30. The tab 60 engages the recess 62. The tab 60 extends radially outward from the recess 62 past an outer circumference of the handle 30. The radially extended portion of the tab 60 slidably engages the groove 58 of the handle sheath 54.

In operation, the engagement of the tab 60 with the recess 62 rotationally secures the blade sheath 42 about the arm 32 of the laryngoscope 28. The engagement of the tab 60 with the groove 58 of the handle sheath 54 vertically secures the handle sheath 54 about the handle 30. The engagement of the blade sheath 42 and the handle sheath 54 creates a fluid resistive or fluid impervious seal such that the disposable or reusable blade sheath 42 and handle sheath 54 protect the arm 32 and handle 30 of the laryngoscope 28 from contamination by exposure to pathogens or other bodily fluid from contact with the patient. By limiting the exposure to pathogens and bodily fluid to the disposable or reusable blade sheath 42 and handle sheath 54, the need to disinfect, such as by autoclaving, the more complex structures, including electronics, of the arm 32 and handle 30, is eliminated or greatly reduced.

Figure 3A:
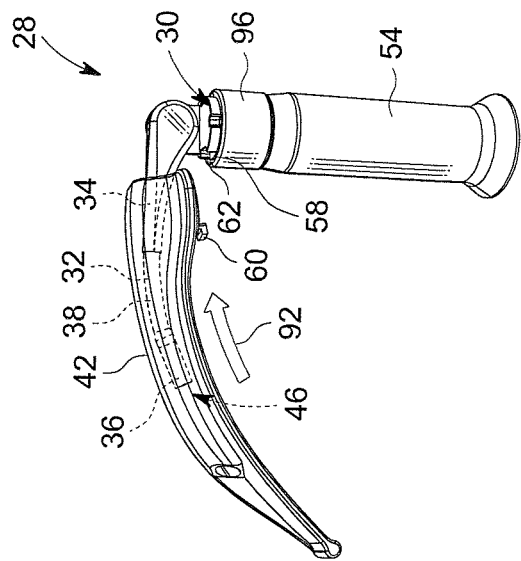
FIG. 3A-D depict the assembly of an embodiment of the laryngoscope.

FIGS. 3A-3D depict in greater detail the assembly of the blade sheath 42 and the handle sheath 54 on the laryngoscope 28. FIG. 3A shows the insertion of the arm 32 into the open end 44 of the blade sheath 42 and into the open interior 46 of the blade sheath 42. The arm 32 is located within the open interior 46 by movement of the blade sheath 42 along the direction represented by arrow 90.

Figure 3B:
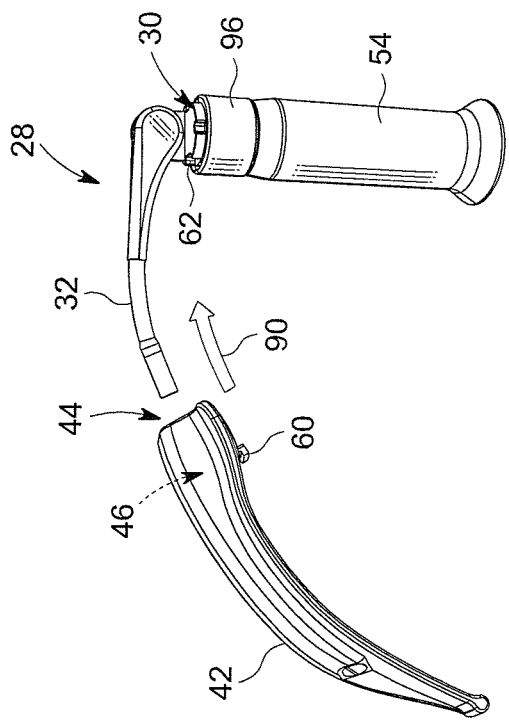

FIG. 3B depicts the arm 32, including the first arm component 34, second arm component 36, and the intermediate arm component 38 disposed within the open interior 46 of the blade sheath 42. The blade sheath 42 is further translated along the arm 32 in the direction of arrow 92.

FIG. C shows the blade sheath 42 completely surrounding the arm 32 and the hinge 40. The blade sheath 42 is placed in this orientation by moving the blade sheath 42 into a furthermost position along arrow 94.

When the blade sheath 42 is in its furthermost position, the distal end 50 of the second arm component 36 is located proximal the window 48. Additionally, the at least one tab 60 on the blade sheath 42 is located within recess 62 of the handle 30. This engagement between the tab 60 and the recess 62 rotationally secures the blade sheath 42 about the arm 32 and handle 30.

Figure 3D:
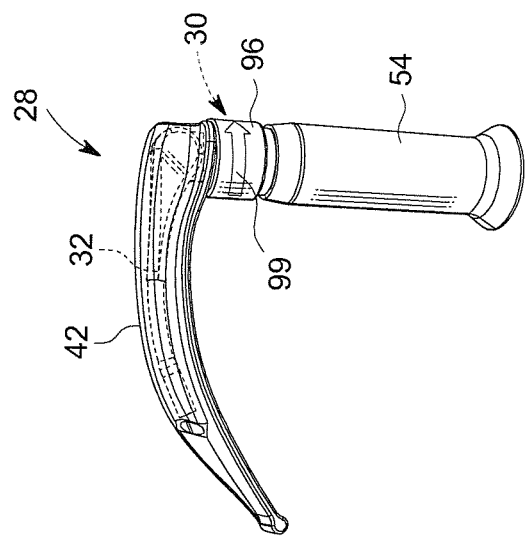
Figure 3C:
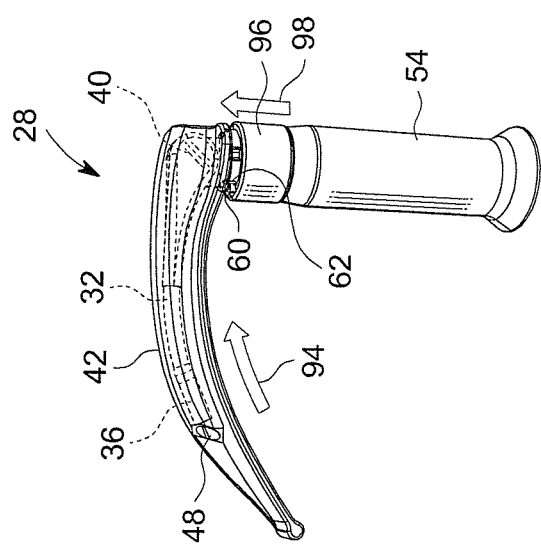

The handle sheath 54 further includes a locking collar 96. The locking collar includes the aforementioned groove 58 which is configured for slidable engagement with the tab 60. As represented by arrow 98, the locking collar is slid about the handle 30 such as to engage the tab 60 with the groove 58. As depicted in FIG. 3D, the locking collar 96 is rotated about the handle 30 in the direction of arrow 99 such that the groove 58 (as better depicted in FIG. 2) is slidably engaged with the tab 60.

This arrangement locks the blade sheath 42 into position about the arm 32 of the laryngoscope 28 and locks the handle sheath 54 in position about the handle 30 and further with respect to the blade sheath 42.

FIGS. 4A-4C depict alternative embodiments of the blade sheath that may be used in connection with embodiments of the laryngoscope 28 disclosed herein.

FIG. 4A depicts a laryngoscope 28 with a handle sheath 54 and a straight blade sheath 64. The straight blade sheath 64 is in the form of a Miller blade, one of the conventional laryngoscope blade constructions. In use, a Miller blade is used during a laryngoscopy by placing the elongated end 52 posterior to the epiglottis. Compressive pressure is applied to the epiglottis with the elongated end 52. This traps the epiglottis, exposing the glottis and vocal chords for visual inspection.

When the laryngoscope 28 is used with a straight blade sheath 64, the arm 32 is configured in a generally straight configuration. The first arm component 34 is pivoted about the hinge 40 such as to form a generally perpendicular angle with the handle sheath 54. The second arm component 36 is also pivoted about the intermediate arm component 38 such as to be in a generally straight alignment with the first arm component 34. In this manner, the shape of the arm 32 is configured to receive and support the straight blade sheath 64.

FIG. 4B depicts a laryngoscope 28 with a handle sheath 54 connected to a generally straight blade sheath 66. The generally straight blade sheath 66 is of the general construction of the conventional Macintosh blade used in direct laryngoscopy. The Macintosh blade construction extends generally perpendicularly from the handle, as with the Miller blade, however, the elongated end 52 of the Macintosh blade is generally curved to a greater extent than is present in a Miller blade. In use during a direct laryngoscopy, the Macintosh blade is placed anterior to the epiglottis of the patient, force applied by the elongated end to the epiglottis raises the epiglottis out of the visual pathway. This permits a clinician to inspect the glottis and vocal chords.

When used with a generally straight blade sheath 66, such as a Macintosh blade, the arm 32 may be configured in a slightly different orientation such as to properly receive and support the generally straight blade sheath 66. When the arm 32 is used with a generally straight blade sheath 66, the first arm component 34 is pivoted about the hinge 40 to form a generally perpendicular angle with the handle sheath 54, as is the case when the laryngoscope 28 is used with a straight blade sheath 64 as in FIG. 4A. The difference in configuration of the laryngoscope 28 when used with a generally straight blade sheath 66 is that the second arm component 36 may be pivoted about the intermediate arm component 38 with respect to the first arm component 34. The second arm component 36 is pivoted downward toward the handle sheath 54. This configuration better matches the curvature of the generally straight blade sheath 66 such that the arm 32 is configured to be better received within the generally straight blade sheath 66 and therefore provides improved rigid support within the straight blade sheath 66.

FIG. 4C depicts a laryngoscope 28 with a handle sheath 54. A curved blade sheath 68 is connected to the handle sheath 54. The curved blade sheath 68 is an embodiment of the blade construction used for a difficult laryngoscopy. The pronounced curve to the blade permits insertion of the blade into the patient's mouth and throat, with minimal movement of the head and neck. In use, the extended end 52 of the curved blade sheath 68 is located anterior to the epiglottis, similar to the use of the Macintosh blade and permits video inspection, as will be disclosed in further detail herein of the glottis and vocal chords of the patient.

When the laryngoscope 28 is to be used with the curved blade sheath 68, the arm 32 is configured for optimal use with the curved blade sheath 68. The first arm component 34 is pivoted about the hinge 40 to form an obtuse angle between the first arm component 34 and the handle sheath 54. As the curved blade sheath 68 operates in a similar manner as to the Macintosh blade to move the epiglottis, the second arm component 36 is pivoted about the intermediate arm component 38 with respect to the first arm component 34 such that a similar angle is presented between the second arm component 36 and the handle sheath 54 when the laryngoscope 28 is used with either the generally straight blade sheath 66 (FIG. 4B) and the curved blade sheath 68 (FIG. 4C).

In an embodiment, the angles between the second arm component 36 and the handle sheath 54 are the same in both the embodiments of FIGS. 4B and 4C. The arm 32 as described above with respect to FIG. 4C and used with a curved blade sheath 68 is configured such that the arm 32 may be received within the curved blade sheath 68, and also that the substantially rigid first arm component 34 and the substantially rigid second arm component 36 are located at positions within the curved blade sheath 68 such as to provide strength and rigidity to the curved blade sheath 68, when in use.

While the three blade sheath embodiments depicted in FIGS. 4A-4C depict three generalized types of blade sheaths, one of ordinary skill in the art would recognize that varying sizes, constructions, and proportions of blade sheaths beyond those disclosed herein may be used by a clinician dependent upon the situation and patient. A non-limiting list of factors that may determine the size and configuration of the blade sheath, includes: patient head and neck mobility, gender, age, and size. Therefore, a laryngoscope blade must be selected for a dimension and qualities that may be suitable to use with a particular patient and a particular situation.

Figure 5:
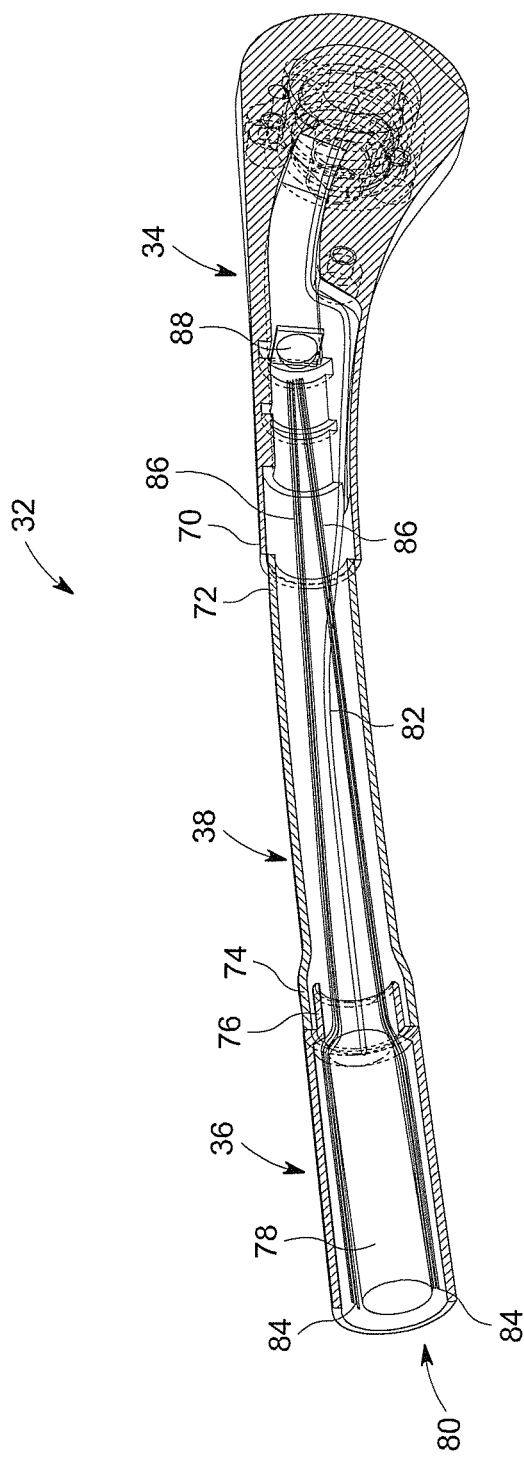
FIG. 5 is a cut away view of an arm of an embodiment of a laryngoscope.

FIG. 5 is a cut away view of an arm 32 of an embodiment of a laryngoscope. The arm 32 includes a substantially rigid first arm component 34, a substantially rigid second arm component 36, and an intermediate portion 38 that movably connects the first arm component 34 to the second arm component 36. In the embodiment depicted in FIG. 4, the intermediate component 38 is flexible, such that the second arm component 36 is movable with respect to the first arm component 34. In a further embodiment, the intermediate arm component 38 is resiliently flexible, such that a predetermined threshold amount of force is required to flex the intermediate arm component 38 to a first position, and a similar threshold force is required to move the arm component to a second position.

A distal end 70 of the first arm component 34 is connected to a proximal end 72 of the intermediate arm component 38 in a coaxial connection. However, it is understood that alternative embodiments may make this connection in a variety of other manners, including, but not limited to screw fit, friction fit, and ultrasonic welding. Alternatively, the first arm component 34 and the intermediate arm component 38 may be integral.

A distal end 74 of the intermediate arm component 38 is connected to a proximal end 76 of the second arm component 36. The connection between the intermediate arm component 38 and the second arm component 36 embodies a coaxial connection, however, it is recognized that alternative connections, as discussed above, may be suitably used. Alternatively, the intermediate arm component 38 may be integral with the second arm component 36. A camera 78 is located at the distal end 80 of the second arm component 36. The camera 78 may be any suitable type of camera for use in a video laryngoscopy procedure. Examples of such suitable cameras may be, but not limited to, a charge coupled device (CCD) camera or a complimentary metal oxide semiconductor (CMOS) camera. The camera 78 captures video imagery from within the throat of the patient and transmits the video image data along wire 82. The wire 82 may extend the length of the arm 32 (e.g. through the second arm component 36, intermediate arm component 38, and first arm component 34) and the hinge (not depicted) into the handle (not depicted) as will be described in greater detail herein.

In an alternative embodiment (not depicted), the second arm component may be constructed with physically smaller dimensions. In order to decrease the dimensions of the second arm component, the camera may be moved away from the tip towards the handle of the laryngoscope. In one embodiment, the camera may be located near the light source 88 (FIG. 5). Fiber optic filaments such as used in an image guide connect the camera to the distal end 80 of the second arm component. In this construction, the second arm component only needs to be of a suitable dimension to hold a bundle of light guiding filaments 86 and a bundle of image guiding filaments.

Additionally, at least one light source 84 is located at the distal end 80 of the second arm component 36. In the embodiment depicted, the at least one light source 84 is the illuminescent ends of fiber optic filaments 86. The fiber optic filaments 86 may extend along some or all of the arm 32 from a secondary light source such as an LED 88. Alternatively, the at least one light source 84 may be an LED itself disposed at the distal end 80 of the second arm component 36.

FIG. 6 depicts an alternative embodiment of the laryngoscope 100. The laryngoscope 100 includes an arm 102 and a handle 104. It should be noted that in this embodiment, the handle 104 includes a handle sheath 106 that secures to the handle 104 in any of known available manners, including a screw engagement or a friction fit, or any other suitable engagement as would be recognized by one of ordinary skill in the art. Alternatively, it is understood that handle sheaths such as described with respect to FIGS. 3A-3D, may be used with the embodiments of the laryngoscope 100.

The arm 102 includes a first arm component 108 and a second arm component 110. The first arm component 108 and the second arm component 110 are pivotably connected by an intermediate arm component 112. In this embodiment, the intermediate arm component 112 is a hinge or other pivotable component. The intermediate arm component 112 may rigidly connect the first arm component 108 to the second arm component 110 in a pivotable relationship. The first arm component 108 and the second arm component 110 are of a substantially rigid construction and the second arm component 110 is able to pivot with respect to the first arm component 108 about the intermediate arm component 112.

The intermediate arm component 112 may further be configured such as to releasably lock in one or more positions defining angles between the second arm component 36 and the first arm component 34. Such a releasably locking intermediate component 112 may be constructed using pins, tabs, springs, gears, or a combination thereof, or any other construction as would be recognized by one of ordinary skill.

Figure 6A:
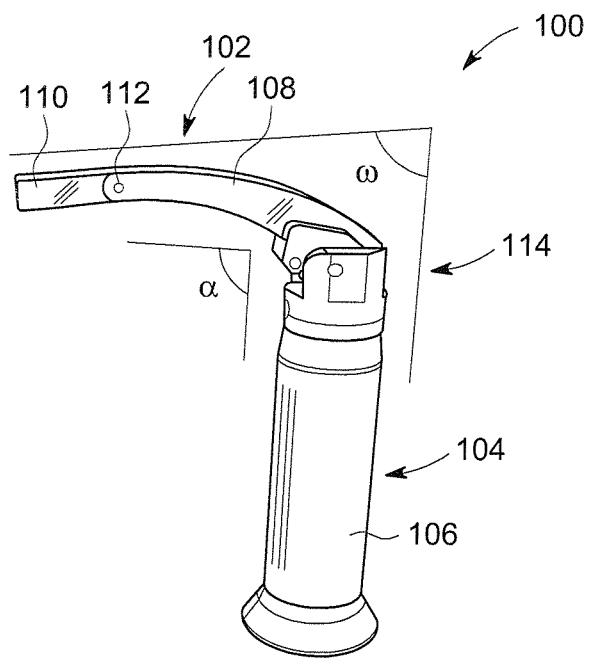
FIG. 6 depicts an alternative embodiment of a laryngoscope.
Figure 6B:
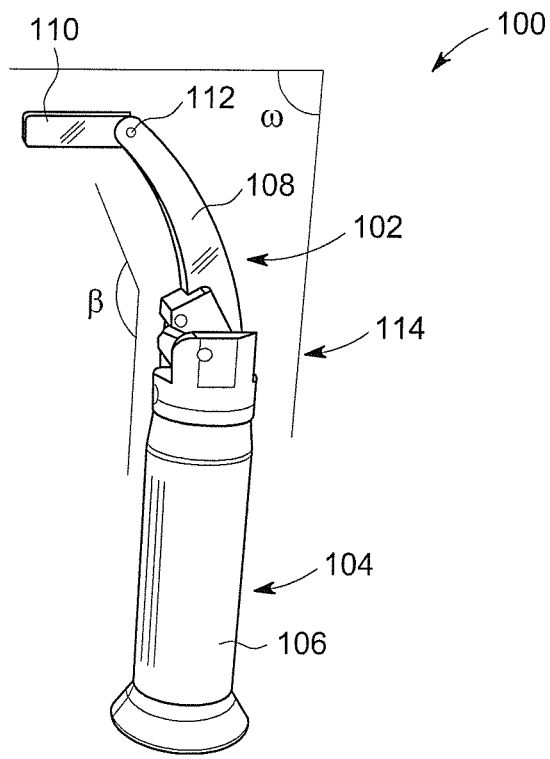

The laryngoscope 100 further comprises a hinge 114 that forms a pivotable connection between the first arm component 108 and the handle 104. The hinge 114 facilitates the first arm component 108 to pivot with respect to the handle 104 between a first position as shown in FIG. 6A and a second position as shown in FIG. 6B. While FIGS. 6A and 6B are herein described as a first position and a second position, it is understood that the hinge 114 is pivotable through a range of positions defined by the geometry between the first arm component 108 and the handle 104.

The respective geometries formed between the arm 102 and the handle 104 of the laryngoscope 100 are depicted in the first position of FIG. 6A and the second position of FIG. 6B. FIG. 6A depicts a flat geometry, such as is used in a direct laryngoscopy, which may be performed using a Macintosh blade or a Miller blade. In the flat geometry, the angle between the first arm component 108 and the handle 104, as represented by angle α is approximately 90°. However, in alternative embodiments, it is to be recognized that angle α may be between approximately 90° and approximately 130°.

FIG. 6B depicts an angled geometry embodied by the first arm component being in the second position and forming an obtuse angle β with respect to the handle 104. The obtuse angle β is generally between 130° and 170°.

Te hinge 114 includes a locking mechanism 116 that releasably secures the first arm component 108 in the first position or in the second position. In an alternative embodiment, the locking mechanism 116 of the hinge 114 may lock the first arm component 108 in a plurality of positions between angles α and β. As with the intermediate arm component 112, the locking mechanism 116 may use a variety of components, including pins, tabs, springs, gears, or any other construction as may be recognized as suitable in construction a releasable locking mechanism.

In an embodiment, the hinge 114 and the locking mechanism 116 may cooperate during use of the laryngoscope 100 to provide repositioning of the angle between the first amnn component 108 and the handle 104. In one use, this may allow for fine tuning or adjustment of the laryngoscope geometry during the laryngoscope procedure. The fine tuning or adjustment may better align the arm 102 within the throat of the patient or direct or focus the camera towards a physiological structure. In an alternative use, the geometry of the laryngoscope 100 may be adjusted intra-procedure to a new geometry between the first arm component 108 and the handle 104 about the hinge 114 and locked into place by locking mechanism 116. The new geometry may be selected to better fit within the throat of the patient, apply mechanical pressure, or reposition the camera.

With respect to FIGS. 6A and 6B, it should additionally be noted that in some embodiments of the laryngoscope 100, the intermediate arm component 112 pivots the second arm component 110 with respect to the first arm component 108 as the first arm component 108 is moved from the first position to the second position. An angle ω between the second arm component 110 and the handle 104 therefore remains substantially the same whether the first arm component 108 has been rotated to the first position or the second position. In one embodiment, such a relation between the second arm component 110 and the handle 104 is maintained by a tie-rod or tie cord (not depicted) connecting the intermediate arm component 112 or the second arm component 110 to the hinge 114, locking mechanism 116, or the handle 104.

Figure 7:
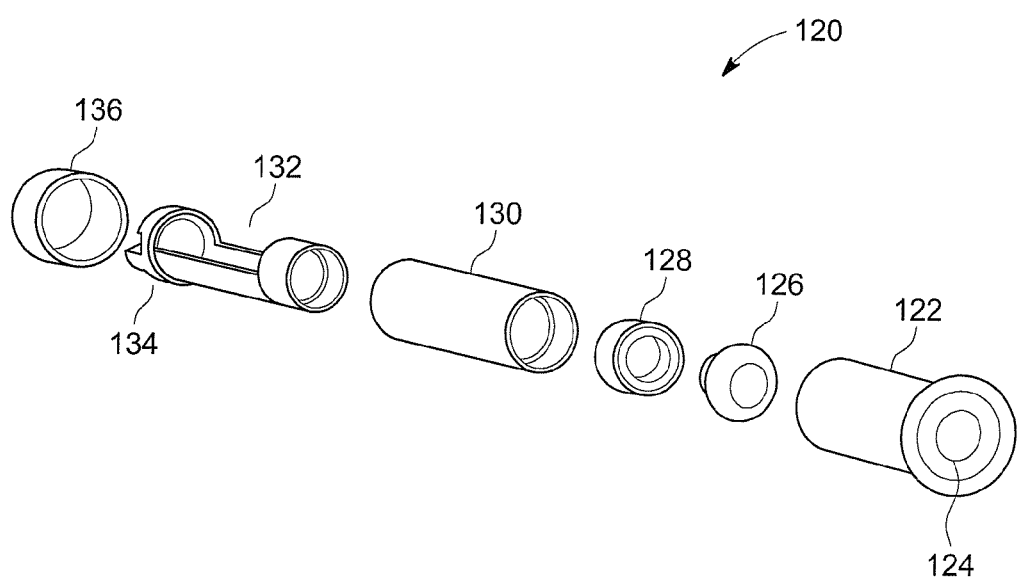
FIG. 7 is an exploded view of a handle of a laryngoscope.

FIG. 7 is an exploded view of an embodiment of the handle 120. The handle 120 includes the handle sheath 122. As described above, the handle sheath 122 may be of a disposable or reusable construction and if the handle sheath 122 is of a reusable construction, then the handle sheath 122 is autocleavable. The handle sheath 122 includes an opening 124 in a bottom end. A data connection 126 is disposed within the handle sheath 122 and extends through the opening 124. The data connection is any such suitable connection for a data transmission line such that the video images may be transmitted from the camera (not depicted) back to a graphical display (FIG. 1). Alternatively, the data connection 126 may be a wireless transmitter. Electronics 128 are disposed in a package around the data connection 126. The electronics 128 may include circuitry and/or a processor configured with a computer readable code such as to control the camera and light source (not depicted) as well as to control the transmission of data by the data connection 126 and to perform basic signal processing.

The handle 120 further includes a handle cylinder 130 which provides both strength and rigidity to the handle 120 as well as protection to the electronics 128 and data connection 126 from physical damage. A battery chamber 132 holds a battery (not depicted) from which the electrical components of the laryngoscope draw power. The battery may be disposable or rechargeable. In the embodiment of the handle 120 of FIG. 7, the battery chamber further includes an integral hinge 134 to which the first arm component (not depicted) is connected. However, an alternative embodiment may locate the hinge 134 as part of the handle cylinder 130 rather than the battery chamber 132. Lastly, the handle 120 includes a locking collar 136, the structure and operation of which has been described in further detail with respect to FIG. 3.

Figure 8:
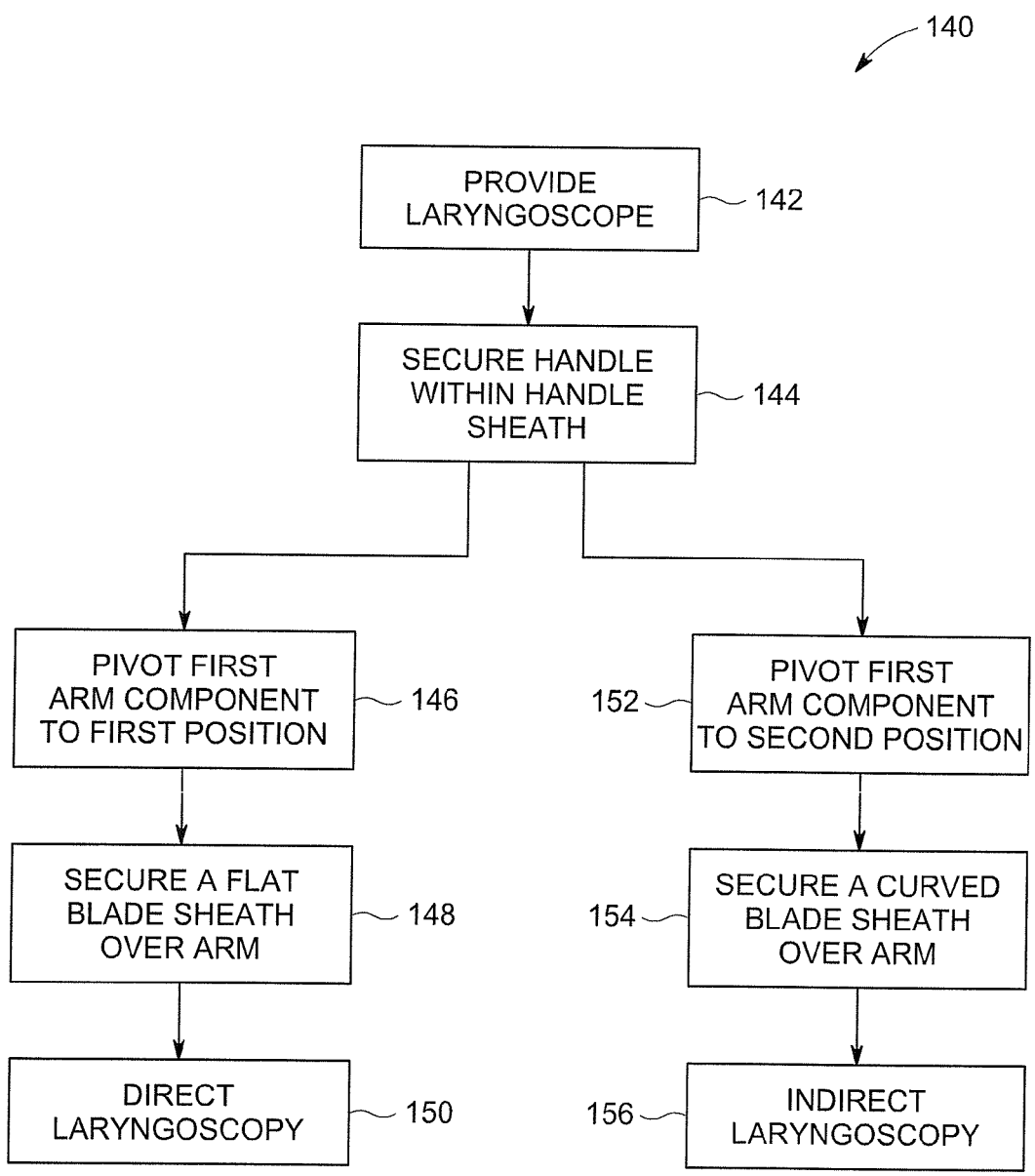
FIG. 8 is a flow chart of a method of configuring a laryngoscope.

FIG. 8 is a flow chart depicting a method of configuring a laryngoscope for performing a laryngoscopy 140. It is understood that the laryngoscope will be configured to perform a selected type of laryngoscopy based upon a clinical preference, a medical condition of the patient, and a physiology of the patient. First, a laryngoscope is provided at 142. The laryngoscope includes a handle, a hinge connected to the handle, a first arm component pivotably connected to the hinge, and a second arm component pivotably connected to the first arm component. Additionally, the laryngoscope may include one or both of a camera and a light source. The camera and/or the light source may be mounted to a distal end of the second arm component.

The handle of the laryngoscope is secured within a handle sheath at 144. The handle sheath may be a disposable or reusable component and forms a fluid impervious barrier around the handle. Embodiments of the handle sheath may be secured to the handle by tab and slot engagement or friction fit. Alternatively, the handle sheath may be secured to the handle by a screw fit.

Next, if the laryngoscopy to be performed is a direct laryngoscopy, then the first arm component of the laryngoscope is pivoted to a first position with respect to the handle. The first position establishes a generally perpendicular geometry between the first arm component and the handle. While the geometry between the first arm component and the handle is generally perpendicular, it is understood that this generally perpendicular geometry includes a range of angles between the first arm component and the handle from about 90° to about 130°. In some embodiments, the hinge may include a locking mechanism that releasably secures the first arm component after it has been pivoted into the first position.

After the first arm component has been pivoted into the first position at 146, in 148 a generally flat blade sheath is secured over the arm of the laryngoscope. The generally flat blade sheath may be selected from a plurality of blade sheaths. The generally flat blade sheath may be selected based upon the size, age, and gender of the patient, or based upon other considerations. The generally flat blade sheath may be disposable or reusable and constructed of a biocompatible plastic material. If the flat blade sheath is reusable, then it is preferably autocleavable. The generally flat blade sheath may be secured over the arm by an attachment to the handle, such as by tabs, friction fit, or a screw fit. Alternatively or in combination, the flat blade sheath may be secured directly to the handle sheath to form a fluid impervious seal about the laryngoscope. The generally flat blade sheath is recognized as a blade sheath that secures about the arm when the first arm component is in the generally perpendicular geometry. The generally flat blade sheath, therefore, includes both Miller and Macintosh blade sheath configurations, as well as others as recognized by one of ordinary skill.

After the flat blade sheath has been secured over the arm at 148, the laryngoscope is configured for use in a direct laryngoscopy 150.

Alternatively, if the laryngoscope is to be used in an indirect laryngoscopy, after the handle is secured within the handle sheath at 144, the first arm component is pivoted to a second position with respect to the handle at 152. The second position establishes a generally obtuse geometry between the first arm component and the handle. While the second position is described as a generally obtuse geometry, it is understood that this includes angles between the first arm component and the handle in the range between 90° and 180°, and in a more specific embodiment, in the range between about 130° to about 170°.

In some embodiments, the hinge may include a locking mechanism that releasably secures the first arm component in the generally obtuse geometry once the first arm component has been pivoted into the second position.

At 154, a curved blade sheath is secured over the arm. The curved blade sheath may be selected from a plurality of blade sheaths based upon an identified laryngoscopy procedure to be performed, in this case an indirect laryngoscopy. Additionally, the curved blade sheath may be selected based upon the size, age, or gender of the patient, or other considerations that may be recognized by one of ordinary skill in the art.

The curved blade sheath may be disposable or reusable and constructed of a biocompatible and fluid impervious material. If the curved blade sheath is reusable, then it is preferably autocleavable. The curved blade sheath may be secured over the arm using a tab, friction fit, or screw fit connection directly with the handle. Alternatively or in conjunction, the curved blade sheath may be secured directly to the handle sheath. One such embodiment may be the locking collar as described above with respect to FIG. 3. If the curved blade sheath is secured directly to the handle sheath, the engagement of the curved blade sheath and the handle sheath preferably forms a fluid impervious seal around the laryngoscope. After the curved blade sheath is secured over the arm at 154, then the laryngoscope is configured for use in performing an indirect laryngoscopy 156.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A laryngoscope comprising:
a handle having a handle axis;
a first arm component having a proximal end and a distal end opposed from the proximal end, the first arm component being substantially rigid;
a second arm component having a proximal end and a distal end opposed from the proximal end, the second arm component being substantially rigid;
an intermediate arm component that movably connects the distal end of the first arm component to the proximal end of the second arm component, a length of the intermediate arm component from a proximal end of the intermediate arm component to a distal end of the intermediate arm component greater than a length of the second arm component from the proximal end of the second arm component to the distal end of the second arm component, a length of the first arm component from the proximal end of the first arm component to the distal end of the first arm component greater than or equal to the combined length of the intermediate arm component and the length of the second arm component; and
a hinge pivotably connecting the handle to the proximal end of the first arm component, the first arm component and the handle being pivotable about the hinge between a first position and a second position;
wherein when the hinge is in the first position, an angle formed between the first arm component and the handle axis is generally perpendicular and when the hinge is in the second position, the angle formed between the first arm component and the handle axis is generally obtuse.

2. The laryngoscope of claim 1, further comprising:
a plurality of blades, each of the plurality of blades comprising:
an open end configured to coaxially receive the first and second arm components; and
an elongated end opposite the open end, the elongated end extending past the distal end of the second arm component.

3. The laryngoscope of claim 2, wherein at least one of the plurality of blades comprises a flat geometry and is configured to coaxially receive the first and second arm components when the hinge is in the first position.

4. The laryngoscope of claim 3, wherein the at least one of the plurality of blades is a Miller blade.

5. The laryngoscope of claim 3, wherein the at least one of the plurality of blades is a Macintosh blade.

6. The laryngoscope of claim 2, wherein at least one of the plurality of blades comprises a curved geometry.

7. The laryngoscope of claim 1, further comprising a lock configured about the hinge to releasably lock the hinge in the first position or the second position.

8. The laryngoscope of claim 7, wherein the first arm component and the handle are pivotable about the hinge to a plurality of positions between the first position and the second position, and the lock releasably locks the first arm component and the handle in the plurality of positions.

9. The laryngoscope of claim 8, wherein the first arm component is pivotable about the hinge while the laryngoscope is in use.

10. The laryngoscope of claim 1, further comprising a light source disposed at the distal end of the second arm component.

11. The laryngoscope of claim 1, wherein when the hinge is in the first position, an angle between the first arm component and the handle axis is between 90 degrees and 130 degrees.

12. The laryngoscope of claim 1, wherein when the hinge is in the second position, an angle between the first arm component and the handle axis is between 130degrees and 170 degrees.

13. The laryngoscope of claim 1, wherein an angle between the second arm component and the handle axis is about 90 degrees or less.

14. The laryngoscope of claim 13, wherein the hinge and the intermediate arm component move in unison when the hinge moves from the first position to the second position, such that the angle between the second arm component and the handle axis is maintained between the first position and the second position.

15. A laryngoscope comprising:
a substantially rigid handle;
a first arm component having a proximal end and a distal end opposed from the proximal end, the first arm component being substantially rigid;
a second arm component having a proximal end and a distal end opposed from the proximal end, the second arm component being substantially rigid;
an intermediate arm component that movably connects the distal end of the first arm component to the proximal end of the second arm component;

a hinge that pivotably connects the handle to the proximal end of the first arm component, the first arm component being pivotable about the hinge between a first position and a second position, wherein the hinge and the intermediate arm component move in unison when the hinge moves from the first position to the second position, such that the angle between the second arm component and the handle is maintained between the first position and the second position;

a removable blade sheath configured with an open interior for receiving the second arm component, intermediate arm component, first arm component, and hinge, the removable blade sheath engages the substantially rigid handle to secure the removable blade sheath about the second arm component, intermediate arm component, first arm component, and hinge.

16. The laryngoscope of claim 15, further comprising:
a power source housed within the open interior of the substantially rigid handle;
a light source disposed at the distal end of the second arm component, the light source electronically coupled to the power source.

17. The laryngoscope of claim 15, wherein the removable blade sheath forms a fluid impervious seal about at least the second arm component, intermediate arm component, and first arm component.

18. The laryngoscope of claim 15, further comprising a handle sheath with an open interior and the handle is disposed with the open interior, wherein the removable blade sheath engages the handle by engaging the handle sheath.

19. A laryngoscope comprising:
a handle;
a first arm component having a proximal end and a distal end opposed from the proximal end, the first arm component being substantially rigid;
a second arm component having a proximal end and a distal end opposed from the proximal end, the second arm component being substantially rigid;
an intermediate arm component that movably connects the distal end of the first arm component to the proximal end of the second arm component;
a plurality of blades, each of the plurality of blades comprising:
an open end configured to coaxially receive the first and second arm components; and
an elongated end opposite the open end, the elongated end extending past the distal end of the second arm component; and
a hinge pivotably connecting the handle to the proximal end of the first arm component, the first arm component and the handle being pivotable about the hinge between a first position and a second position;
wherein when the hinge is in the first position, an angle formed between the first arm component and the handle is generally perpendicular and when the hinge is in the second position, the angle formed between the first arm component and the handle is generally obtuse.

20. The laryngoscope of claim 19, wherein the hinge and the intermediate arm component move in unison when the hinge moves from the first position to the second position, such that an angle between the second arm component and the handle is maintained between the first position and the second position.

* * * * *